(12) United States Patent
Hradil et al.

(10) Patent No.: US 8,487,113 B2
(45) Date of Patent: Jul. 16, 2013

(54) METHOD FOR THE PREPARATION OF TIZANIDINE HYDROCHLORIDE

(75) Inventors: Pavel Hradil, Hlusovice (CZ); Lubomir Kvapil, Slatinice (CZ); Martin Grepl, Hlusovice (CZ); Jan Novotny, Olomouc (CZ)

(73) Assignee: Farmak, A.S., Olomouc (CZ)

( * ) Notice: Subject to any disclaimer, the term of this patent is extended or adjusted under 35 U.S.C. 154(b) by 0 days.

(21) Appl. No.: 13/131,269

(22) PCT Filed: Dec. 18, 2009

(86) PCT No.: PCT/CZ2009/000158
§ 371 (c)(1),
(2), (4) Date: Jun. 23, 2011

(87) PCT Pub. No.: WO2010/069280
PCT Pub. Date: Jun. 24, 2010

(65) Prior Publication Data
US 2011/0263863 A1    Oct. 27, 2011

(30) Foreign Application Priority Data

Dec. 18, 2008    (CZ) .................................... 2008-819

(51) Int. Cl.
*C07D 285/06*    (2006.01)
(52) U.S. Cl.
USPC ...................... 548/127; 548/311.7; 548/312.1
(58) Field of Classification Search
USPC .................... 548/127, 311.7, 312.1
See application file for complete search history.

(56) References Cited

U.S. PATENT DOCUMENTS
3,843,668 A    10/1974    Neumann

FOREIGN PATENT DOCUMENTS

| CA | 1299576 | * | 4/1992 |
|----|---------|---|--------|
| CH | 579565 | | 3/1973 |
| CZ | 286717 | | 6/2000 |
| EP | 644192 | | 3/1995 |
| RU | 223506 | | 8/2004 |
| WO | WO 2008008394 | | 1/2008 |
| WO | WO 2008008394 A1 | * | 1/2008 |

OTHER PUBLICATIONS

International Search Report, mailed Jun. 17, 2011, for PCT International Application No. PCT/CZ2009/000158.

* cited by examiner

*Primary Examiner* — Yong Chu
(74) *Attorney, Agent, or Firm* — Pearl Cohen Zedek Latzer, LLP

(57) ABSTRACT

The invention deals with a preparation method of salts of 5-chloro-4-(2-imidazolin-2-yl-amino)-2,1,3-benzothiadiazole (tizanidine) of formula I, especially tizanidine hydrochloride, comprising preparation of a salt of tizanidine of formula I and a carboxylic acid as an intermediate, from which, after acidification with hydrogen chloride, tizanidine hydrochloride is obtained in a high yield and purity.

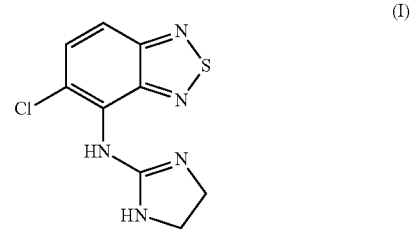

(I)

11 Claims, No Drawings

METHOD FOR THE PREPARATION OF TIZANIDINE HYDROCHLORIDE

CROSS-REFERENCE TO RELATED APPLICATIONS

This application is a National Phase Application of PCT International Application No. PCT/CZ2009/000158, International Filing Date Dec. 18, 2009, entitled "A Method for the Preparation of Tizanidine Hydrochloride", published on Jun. 24, 2010, as International Publication No. WO 2010/069280, which claims priority from Czech Republic Patent Application No. PV 2008-819, filed Dec. 18, 2008, both of which are incorporated herein by reference in their entirety.

TECHNICAL FIELD

The invention deals with a method for the preparation of salts of 5-chloro-4-(2-imidazolin-2-yl-amino)-2,1,3-benzothiadiazole (tizanidine) of formula I, especially of tizanidine hydrochloride.

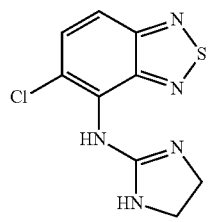

(I)

Tizanidine hydrochloride is pharmacologically characterized as a centrally acting antagonist of $\alpha_2$ adrenergic receptors that inhibits releasing of norepinephrine in the brain and spinal cord. It is used as a spasmolytic agent and a muscle relaxant.

BACKGROUND ART

Several different methods of synthesis of 5-chloro-4-(2-imidazolin-2-yl-amin)-2,1,3-benzothiadiazole, or tizanidine, have been described.

According to the original U.S. Pat. No. 3,843,668 tizanidine is prepared with the use of compounds of general formula IIa,

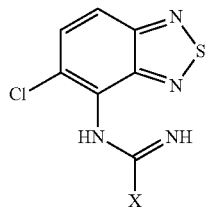

(IIa)

where X represent a reactive removable group —NHNO$_2$, —S—R$_1$, —O—R$_1$ or —NHR$_1$, where R$_1$ means a hydrogen atom or an alkyl with 1 to 3 carbon atoms. This reactive group is substituted by a reaction with ethylene diamine and at the same time cyclization occurs, producing tizanidine.

According to the Swiss method CH 579,565 tizanidine is prepared by cyclization of compounds of general formula IIb,

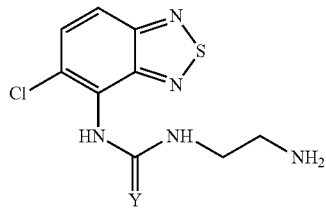

(IIb)

where Y represents an oxygen or sulphur atom, in an inert solvent in the presence of bases (e.g. alkali metal and alkaline earth hydroxides) and of certain compounds of the heavy metals mercury and lead.

According to other methods tizanidine is prepared by means of a reaction of 2-amino-4-chloro-2,1,3-benzothiadiazole of formula (IIc)

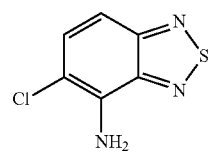

(IIc)

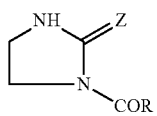

(IId)

with the imidazolidine derivative of formula IId (Z=O) as described in patent no. EP 644 192, or with the derivative IId (Z=S) as specified in the patent no. CZ 286 717, where R represents a hydrogen atom, a substituted or unsubstituted alkyl, cycloalkyl, aryl, aralkyl or alkoxy group.

In these patents dehydrocondensation agents are used for the reaction, such as phosphorus(V) oxychloride, or sulfuric acid, phosphoric acid, sulfuryl chloride, or dicyclohexylcarbodiimide.

A common characteristic of the above mentioned methods of synthesis is that the last steps involve several reactions carried out by mean of reactive agents, which results in contamination of thus prepared tizanidine by a number of chemical impurities, as well as of coloured contaminants that are difficult to remove.

These coloured contaminants, although they are usually present in undetectable quantities, can make the final product, tizanidine hydrochloride in this case, unsatisfactory as regards its appearance or colour of its solution.

Preparation of tizanidine hydrochloride is described in German patent no. DE 3 610 407. The tizanidine base of formula I is dissolved in DMF, filtered with active coal and the filtrate is saturated with gaseous hydrogen chloride at ca. 60° C., producing crude tizanidine hydrochloride. The latter is aspirated and dissolved in a water/ethanol mixture and, after cooling down, tizanidine hydrochloride crystallizes.

According to Russian patent no. RU 2 234 506 concentrated hydrochloric acid is added to a suspension of the tizanidine base in ethanol, the whole is dissolved when hot and, after filtering and cooling down, tizanidine hydrochloride crystallizes.

PCT patent application no. WO 2008/008394 describes the preparation of various forms of tizanidine succinate by mixing of the tizanidine base with succinic acid or by mixing of tizanidine hydrochloride with the sodium salt of succinic acid.

Disadvantages of the Above Mentioned Methods:

pure tizanidine base is often used as the starting material, which must be first prepared, most frequently by crystallization;

Obtaining the pure base is demanding for time and energy. During crystallization its losses occur, during dissolving or concentration of solutions it is subject to thermal exposure, which produces impurities;

Another common disadvantage is a relatively low solubility of tizanidine base and tizanidine hydrochloride in commonly used solvents that are described in the above-mentioned patents.

The authors of the present invention have found out that for crystallization of the tizanidine base in methanol, as described e.g. in U.S. Pat. No. 3,843,668, at least 37 ml of methanol must be used for dissolution of 1 g of the tizanidine base.

Similarly, to achieve crystallization of tizanidine hydrochloride, as described e.g. in patent no. EP 644 192, at least 43 ml of ethanol must be used for dissolution of 1 g of tizanidine hydrochloride.

In order to eliminate the above mentioned disadvantages the authors of the present invention have performed extensive research with the following results. During the preparation of tizanidine hydrochloride a number of hitherto unknown dependencies have been discovered.

DISCLOSURE OF INVENTION

We have found out that the tizanidine base, which is very poorly soluble in commonly used solvents, such as alcohols and ketones, dissolves well after addition of carboxylic acids. From a solution produced this way a salt of tizanidine with the corresponding carboxylic acid can be obtained. By dissolution of this salt and acidification of the resulting solution with hydrogen chloride tizanidine hydrochloride can be obtained in a high yield and purity.

For example, mixing of 1 g of the tizanidine base with 4 ml of methanol and heating to the boiling point will produce a suspension, to which an addition of only 0.45 ml of acetic acid is sufficient to obtain a solution.

Similarly, mixing of 1 g of the tizanidine base with 4 ml of methanol and heating to the boiling point will produce a suspension, to which an addition of only 0.9 ml of acetic acid is sufficient to obtain a solution.

The authors of the present invention have made a comparison of the yield and purity of tizanidine hydrochloride prepared in accordance with the present invention, example 1, with those prepared in accordance with German patent no. DE 3 610 407 and with Russian patent no. RU 2 234 506. An identical starting tizanidine base having the purity of 99.15 HPLC was used in all the experiments.

The yields are related to the starting tizanidine base in all the cases. The purity of the prepared products was evaluated by means of HPLC and also by comparison of colour of the solutions of prepared products by means of the GY scale in accordance with European Pharmacopoeia 2005 (Art. 2.2.1. and 2.2.2., the GY scale consisting of seven tones from GY1 to GY7, GY1 being the yellowest solution and GY7 being the least yellow one).

TABLE NO. 1

|  | Yield [%] | HPLC purity [%] | GY colour |
| --- | --- | --- | --- |
| DE 3 610 407 | 76.6 | 99.98 | 5 |
| RU 2 234 506 | 79.2 | 99.99 | 5 |
| Present patent | 87.5 | 99.99 | 7 |

The table shows that HPLC purity is nearly the same in all the three cases and it nearly approximates 100%. The appearance of the solutions exhibits great differences. In the case of the German and Russian patents the colour of the solutions is GY5, i.e. yellowish solutions prepared from visibly yellow products. In the case of the present patent the colour is GY7, i.e. very slightly yellowish solution that was prepared from nearly colourless tizanidine hydrochloride.

The invention provides a method for the preparation of tizanidine hydrochloride from the tizanidine base, which method comprises the following operations:

a) mixing the tizanidine base, a carboxylic acid and optionally an inert solvent;
b) preparing a solution of the tizanidine carboxylic acid salt;
c) isolation of the tizanidine carboxylic acid salt;
d) dissolution of the tizanidine carboxylic acid salt in a mixture of a carboxylic acid and optionally an inert solvent;
e) acidifying the solution of the tizanidine carboxylic acid salt using hydrogen chloride;
f) isolation of tizanidine hydrochloride.

First, a solution of a salt of tizanidine with a carboxylic acid is prepared by means of the corresponding carboxylic acid and tizanidine base. This tizanidine carboxylic acid salt can either be isolated, redissolved and converted to tizanidine hydrochloride by addition of hydrogen chloride. Or it is possible to add hydrogen chloride directly to said solution of the tizanidine carboxylic acid salt and thus to obtain directly, "one pot", tizanidine hydrochloride. Preparations of these salts can be carried out either solely in an excess of the carboxylic acid, which serves as the solvent at the same time, or it is possible to use the carboxylic acid in combination with an inert organic solvent. Further, it is also possible to use a different carboxylic acid to dissolve the tizanidine carboxylic acid salt, said different carboxylic acid preferably being acetic, formic or propionic acid.

The carboxylic acids that can be used include unsubstituted $C_1$ to $C_6$ carboxylic acids such as formic, acetic, propionic up to hexanoic acids.

Further suitable carboxylic acids include those substituted with one or more halogen atoms in their chain, e.g. monochloroacetic or dichloroacetic acids.

Other suitable carboxylic acids include those substituted with the —OH group in their chain, such as glycolic acid, or carboxylic acids substituted with an —O—R group, where —R represents a $C_1$ to $C_4$ alkyl, in their chain, such as ethoxyacetic acid.

It is well known that at least an equivalent quantity of the corresponding acid must be used for the preparation of a salt from a base. The authors of the present invention have found out that salts of tizanidine with carboxylic acids can be prepared in a wide range of molar ratios of the tizanidine base: carboxylic acid, preferably from 1:1 to 1:20, more preferably from 1:1.5 to 1:10.

Inert solvents that can be used include $C_1$ to $C_4$ alcohols, such as methanol, ethanol, isopropyl alcohol and n-butanol, and also their esters, such as ethyl acetate, or ketones such as acetone or methyl ethyl ketone. However, other types of solvents that are commonly used in organic chemistry for preparation of salts can also be used in principle.

As hydrogen chloride, gaseous hydrogen chloride can be used, but for practical reasons it is more convenient to use a solution thereof, e.g. in isopropyl alcohol.

The prepared tizanidine carboxylic acid salts are generally well crystallizing and filterable crystalline substances that can be relatively easily isolated from their solution by suitable selection of crystallization conditions (inert solvent, amount of the carboxylic acid used and crystallization temperature).

Preparation of the Solution of the Tizanidine Carboxylic Acid Salt can be Made in a usual manner, e.g. by heating of a mixture of the tizanidine base, the acid and optionally a solvent, conveniently to a temperature in the range from the room temperature to the boiling temperature of the mixture, preferably to 70-80° C. The resulting tizanidine acid salt is then crystallized, preferably by cooling down, e.g. to a temperature between 0 and 5° C., and isolated by usual methods.

Preparation of the Tizanidine Carboxylic Acid Salts can Provide a High Purifying Effect, it being also possible to achieve high yields by selecting the crystallization conditions.

The present invention also describes new salts of tizanidine such as the formate, acetate, propionate, hexanoate, monochloroacetate, dichloroacetate, glycolate and ethoxyacetate. For their characterization the methods of $^1$H and $^{13}$C NMR spectroscopy, X-ray powder diffraction (XRPD) and differential scanning calorimetry (DSC) were used.

The advantages of the present preparation method of tizanidine hydrochloride are as follows:
  it is not necessary to purify the tizanidine base by separate crystallization;
  lower consumption of solvents;
  lower losses of tizanidine;
  high yield at simultaneous high purity of tizanidine hydrochloride.

EXAMPLES

The principle of the procedures according to the invention is explained in a more detailed way in the following examples. These examples have an illustrative character and do not limit the scope of the invention in any respect.

The newly prepared salts of tizanidine in the present invention were characterized with differential scanning calorimetry (DSC) using Perkin Elmer instrumentation, the Pyris Diamond DSC model with evaluation by means of Pyris software, version 5.0. The samples were analyzed in open aluminium pans in a nitrogen atmosphere. The temperature range was set beginning 50° C. and the heating rate was 5° C./min.

NMR spectra were measured by means of the Bruker Avance 300 device at 300 MHz ($^1$H) and 75 MHz ($^{13}$C). The samples were dissolved in DMSO—$d_6$ and measured at 300K.

X-ray powder diffraction was measured with the XRD-7 Seifert Co. device using CuK$_\alpha$ radiation ($\lambda$=1.54178 Å) with the step of 0.02°, integration time of 4 s and the 2Theta range was 4-40°.

Example 1

Preparation of Tizanidine Hydrochloride (Making Use of Isolation of Tizanidine Acetate)

To 60 ml of acetic acid 40 g of the tizanidine base (99.15% HPLC) are gradually added under stirring and heating until a yellow solution is obtained at 70 to 80° C., to which 200 ml of acetone are added. Shortly thereafter crystallization begins. After cooling to 0 to 5° C. and aspiration 47.25 g of tizanidine acetate (i.e. 95.5% th.) are obtained.

DSC exhibits endothermic transition at 166° C. and 224° C.

$^1$H NMR (DMSO-$d_6$, 300 MHz) δ 7.61 (1H, d, J=9.3 Hz), 7.49 (1H, d, J=9.3 Hz), 6.35 (2H, bs), 3.4 (4H, s), 1.9 (3H, s).

$^{13}$C NMR (DMSO-$d_6$, 75 MHz) δ 171.93, 157.95, 154.49, 151.58, 141.17, 132.14, 122.92, 112.23, 41.75, 21.00.

XRPD (2Theta): 10.7, 15.0, 17.6, 20.2, 21.4, 23.1, 24.4, 24.7, 26.2, 35.7, 36.9.

24 g of tizanidine acetate are added to 50 ml of acetic acid. After heating to 70 to 80° C. a solution is obtained, which is diluted with 115 ml of acetone and, after filtration with 2 g of active coal, the hot solution is acidified with 18 ml of isopropanolic hydrogen chloride. Shortly thereafter quick crystallization of tizanidine hydrochloride occurs, which is completed by cooling to 0 to 5° C.

After aspiration 19.4 g of tizanidine hydrochloride (87.5%) are obtained, HPLC purity 99.99%, colour GY7.

DSC exhibits endothermic transition at 287° C. and exothermic transition at 316° C.

Example 2

Preparation of Tizanidine Hydrochloride (without Isolation of Tizanidine Acetate)

12.0 g of the tizanidine base (99.15% HPLC) are added to 26 ml of acetic acid. The resulting suspension is dissolved under stirring and heating at ca. 70 to 80° C. 55 ml of acetone and 1 g of active coal are added to this solution and after stirring for 15 minutes the solution is filtered. The hot filtrate is acidified by addition of 10 ml of isopropanolic hydrogen chloride. Shortly thereafter quick crystallization of tizanidine hydrochloride occurs, which is completed by cooling to 0 to 5° C. After aspiration 13.0 g of tizanidine hydrochloride (i.e. 95.0% th.) are obtained, purity 99.95% HPLC, colour GY6.

Example 3

Preparation of Tizanidine Formate 3.0 g of the tizanidine base (99.15% HPLC) and 1.9 g of 99% formic acid are added to 5 ml of isopropyl alcohol; after short heating to boil a yellowish solution results, from which a precipitated product starts to separate. After cooling to 0-5° C. and aspiration 3.09 g of tizanidine formate are obtained.

DSC exhibits endothermic transition at 179° C. and 207° C. $^1$HNMR (DMSO-$d_6$, 300 MHz) δ 8.17 (1 Hz), 7.65 (1H, d, 0.1=9.3 Hz), 7.55 (1H, d, J=9.3 Hz), 6.62 (2H, bs), 3.40 (4 Hz).

$^{13}$C NMR (DMSO-$d_6$, 75 MHz) δ 163.45, 158.02, 154.44, 151.60, 139.60, 132.05, 123.87, 113.14, 41.83.

XRPD (2Theta): 10.2, 11.2, 12.0, 15.0, 17.8, 18.0, 20.6, 22.0, 22.6, 23.4, 24.2, 24.4, 24.8, 25.7, 26.3, 27.4, 28.7, 29.3, 38.5.

The further processing sequence is similar to that of example 1 with the difference that formic acid and isopropyl alcohol are used for the preparation of a solution of tizanidine formate. The yield is 2.49 g of tizanidine hydrochloride with the purity of 99.98% HPLC, colour GY7.

Example 4

Preparation of Tizanidine Propionate

To 7 ml of isopropyl alcohol, 3.0 g of the tizanidine base (99.15% HPLC) and 2.5 g of propionic acid are added. After brief heating to boil a yellowish solution results, from which a precipitated product starts to separate. After cooling to 0 to 5° C. and aspiration 3.53 g of tizanidine propionate are obtained.

DSC exhibits endothermic transition at 94° C., 148° C. and 217° C.

$^1$H NMR (DMSO-$d_6$, 300 MHz) δ 7.62 (1H, d, J=9.3 Hz), 7.49 (1H, d, J=9.3 Hz), 6.35 (2H, bs), 3.38 (4 Hz), 2.20 (4H, q, J=7.4 Hz), 0.99 (6H, t, J=7.4 Hz).

$^{13}$C NMR (DMSO-$d_6$, 75 MHz) δ 175.10, 157.96, 154.49, 151.59, 141.13, 132.13, 122.95, 112.25, 41.76, 26.83, 9.01.

XRPD (2Theta): 8.3, 10.8, 11.2, 13.8, 17.6, 18.0, 20.2, 21.2, 21.8, 23.8, 25.3, 27.2, 27.6.

The further processing sequence is similar to that of example 1 with the difference that propionic acid and isopropyl alcohol are used for the preparation of a solution of tizanidine propionate. The yield is 2.29 g of tizanidine hydrochloride with the purity of 99.98% HPLC, colour GY7.

Example 5

Preparation of Tizanidine Hexanoate

To 5 ml of ethanol, 3.0 g of the tizanidine base (99.15% HPLC) and 2.5 g of hexanoic acid are added. After brief heating to boil a yellowish solution results, from which a precipitated product starts to separate. After cooling to 0 to 5° C. and aspiration 3.25 g of tizanidine hexanoate are obtained.

DSC exhibits endothermic transition at 116° C. and 208° C.

$^1$H NMR (DMSO-$d_6$, 300 MHz) δ 7.62 (1H, d, J=9.3 Hz), 7.49 (1H, d, J=9.3 Hz), 6.35 (2H, bs), 3.38 (4 Hz), 2.18 (2H, t, J=7.3 Hz), 1.56-1.42 (2H, m), 1.35-1.20 (4H, m), 1.35 (3H, t, J=7.3 Hz).

$^{13}$C NMR (DMSO-$d_6$, 75 MHz) δ 174.42, 157.95, 154.50, 151.58, 141.21, 132.14, 122.90, 112.20, 41.75, 33.57, 30.67, 24.09, 21.73, 13.72.

XRPD (2Theta): 8.2, 12.0, 14.0, 16.2, 18.7, 19.4, 21.7, 22.3, 24.2, 25.0, 26.4, 28.6, 29.0, 34.6.

The further processing sequence is similar to that of example 1 with the difference that formic acid and ethanol are used for the preparation of a solution of tizanidine hexanoate. The yield is 2.15 g of tizanidine hydrochloride with the purity of 99.97% HPLC, colour GY7.

Example 6

Preparation of Tizanidine Glycolate

To a solution of 3.0 g of glycolic acid in 6 ml of ethanol, 3.0 g of the tizanidine base (99.15% HPLC) are added. After brief heating to boil a solution results, from which a crystalline precipitated product starts to separate. After cooling to 0 to 5° C. and aspiration 2.8 g of tizanidine glycolate are obtained.

DSC exhibits endothermic transition at 176° C.

$^1$H NMR (DMSO-$d_6$, 300 MHz) δ 7.64 (1H, d, J=9.3 Hz), 7.54 (1H, d, J=9.3 Hz), 6.55 (2H, bs), 3.88 (2 Hz), 3.38 (4H, s).

$^{13}$C NMR (DMSO-$d_6$, 75 MHz) δ 174.20, 158.01, 154.46, 151.60, 140.06, 132.07, 123.59, 112.88, 59.60, 41.81.

XRPD (2Theta): 9.9, 14.9, 17.3, 18.2, 20.1, 20.3, 20.7, 21.8, 24.0, 24.3, 25.6, 25.9, 27.9, 28.3.

The further processing sequence is similar to that of example 1 with the difference that propionic acid and ethanol are used for the preparation of a solution of tizanidine glycolate. The yield is 2.22 g of tizanidine hydrochloride with the purity of 99.98% HPLC, colour GY6.

Example 7

Preparation of Tizanidine Ethoxyacetate

To a solution of 2.0 g of ethoxyacetic acid in 4 ml of isopropyl alcohol, 3.0 g of the tizanidine base (99.15% HPLC) are added. After brief heating to boil a solution results, from which a crystalline precipitated product starts to separate. After cooling to 0 to 5° C. and aspiration 3.8 g of tizanidine ethoxyacetate are obtained.

DSC exhibits endothermic transition at 141° C.

$^1$H NMR (DMSO-$d_6$, 300 MHz) δ 7.63 (1H, d, J=9.3 Hz), 7.53 (1H, d, J=9.3 Hz), 6.55 (2H, bs), 3.92 (2H, s), 3.48 (2H, q, J=7.1 Hz), 3.39 (4 Hz), 1.10 (3H, t, J=7.2 Hz).

$^{13}$C NMR (DMSO-$d_6$, 75 MHz) δ 171.87, 158.02, 154.46, 151.60, 140.28, 132.09, 123.46, 112.75, 67.29, 65.65, 41.80, 14.88.

XRPD (2Theta): 8.6, 11.4, 11.6, 12.1, 15.3, 16.0, 17.0, 18.3, 18.7, 19.4, 20.4, 21.9, 24.0, 24.8, 25.3, 26.0, 26.3, 26.8, 27.7, 28.0, 34.8.

The further processing sequence is similar to that of example 1 with the difference that acetic acid and isopropyl alcohol are used for the preparation of a solution of tizanidine ethoxyacetate. The yield is 2.81 g of tizanidine hydrochloride with the purity of 99.98% HPLC, colour GY7.

Example 8

Preparation of Tizanidine Monochloroacetate

To a solution of 2.0 g of monochloroacetic acid in 10 ml of isopropyl alcohol 3.0 g of the tizanidine base (99.15% HPLC) are added. After brief heating to boil a solution results, from which a crystalline precipitated product starts to separate. After cooling to 0 to 5° C. and aspiration 3.31 g of tizanidine monochloroacetate are obtained.

DSC exhibits endothermic transition at 133° C. and two exothermic transitions at 135° C. and 145° C.

$^1$H NMR (DMSO-$d_6$, 300 MHz) δ 7.83 (1H, d, J=9.3 Hz), 7.75 (1H, d, J=9.3 Hz), 7.63 (2H, bs), 4.18 (1H, s), 3.55 (4H, s).

$^{13}$C NMR (DMSO-$d_6$, 75 MHz) δ 169.08, 158.19, 154.21, 151.66, 131.67, 127.70, 116.84, 42.17, 42.10.

XRPD (2Theta): 9.6, 10.0, 11.9, 13.0, 13.5, 15.3, 16.5, 16.9, 18.4, 20.2, 20.6, 22.1, 23.9, 24.9, 26.2, 26.6, 27.2, 28.0, 28.3, 30.1, 31.1, 33.5, 37.3, 38.6.

The further processing sequence is similar to that of example 1 with the difference that formic acid and isopropyl alcohol are used for the preparation of a solution of tizanidine monochloroacetate. The yield is 2.42 g of tizanidine hydrochloride with the purity of 99.90% HPLC, colour GY6.

Example 9

Preparation of Tizanidine Dichloroacetate

To a solution of 3.0 g of dichloroacetic acid in 5 ml of isopropyl alcohol, 3.0 g of tizanidine base (99.15% HPLC) are added. After short heating to boil a solution results, from which, after addition of ethyl acetate, a crystalline precipitated product starts to separate. After cooling to 0 to 5° C. and aspiration 4.15 g tizanidine dichloroacetate are obtained.

DSC exhibits endothermic transition at 187° C. and exothermic transition at 190° C.

$^1$H NMR (DMSO-$d_6$, 300 MHz) δ 8.65 (2H, bs), 8.07 (1H, d, J=9.3 Hz), 7.87 (1H, d, J=9.3 Hz), 6.10 (1 Hz), 3.65 (4H, s).

$^{13}$C NMR (DMSO-$d_6$, 75 MHz) δ 166.12, 158.49, 154.02, 151.73, 131.34, 131.15, 127.37, 120.18, 69.67, 42.49.

XRPD (2Theta): 10.3, 12.3, 12.8, 18.2, 19.1, 19.6, 21.2, 21.7, 22.2, 22.8, 24.8, 25.9, 27.3, 27.5, 29.7, 32.9.

The further processing sequence is similar to that of example 1 with the difference that propionic acid and isopropyl alcohol are used for the preparation of a solution of tizanidine dichloroacetate. The yield is 2.97 g of tizanidine hydrochloride with the purity of 99.90% HPLC, colour GY6.

Industrial Applicability

The method for the preparation of tizanidine hydrochloride can be applied in convenient technological-economical conditions while maintaining a sufficiently high yield with high purity.

The invention claimed is:

1. A method for the preparation of tizanidine hydrochloride, comprising the following steps:
   a) mixing tizanidine base and a $C_1$ to $C_6$ carboxylic acid in at least a stoichiometric ratio;
   b) preparing a solution of the tizanidine carboxylic acid salt from the mixture obtained in step (a);
   c) acidifying the solution obtained in step (b) with hydrogen chloride; and
   d) isolating the tizanidine hydrochloride.

2. A method for the preparation of tizanidine hydrochloride, comprising the following steps:
   a) mixing tizanidine base and a $C_1$ to $C_6$ carboxylic acid in at least a stoichiometric ratio;
   b) preparing a solution of the tizanidine carboxylic acid salt from the mixture obtained in step (a);
   c) acidifying the solution obtained in step (b) with hydrogen chloride; and
   d) isolating the tizanidine hydrochloride wherein the carboxylic acid is formic, acetic, or propionic up to caproic acids and wherein the carboxylic acid may be substituted with at least one halogen, OH or OR, wherein R is an alkyl.

3. The method according to claim 2, wherein the carboxylic acid is monochloroacetic acid or dichloroacetic acid.

4. The method according to claim 2, wherein the carboxylic acid is glycolic acid.

5. The method according to claim 2, wherein the carboxylic acid is ethoxyacetic acid.

6. The method according to claim 1, wherein the preparation of the solution of the tizanidine carboxylic acid salt is performed in combination with an inert solvent.

7. The method according to claim 6, wherein the inert solvent is methanol, ethanol or 2-propanol.

8. The method according to claim 6, wherein the inert solvent is ethyl acetate.

9. The method according to claim 6, wherein the inert solvent acetone or methyl ethyl ketone.

10. The method according to claim 1, wherein tizanidine hydrochloride is obtained in a purity of at least 99%.

11. The method according to claim 1, wherein tizanidine hydrochloride is obtained in a purity of at least 99.8%.

* * * * *